United States Patent
Binier

(10) Patent No.: US 9,636,464 B1
(45) Date of Patent: May 2, 2017

(54) DRUG DELIVERY DEVICE AND A DRUG INFORMATION DETECTION DEVICE

(71) Applicant: INNOVATIVE PRECISION INSTRUMENTS LIMITED, Hong Kong (HK)

(72) Inventor: Richard Jean Marie Binier, Hong Kong (HK)

(73) Assignee: Innovative Precision Instruments Limited, Hong Kong (CN)

( * ) Notice: Subject to any disclaimer, the term of this patent is extended or adjusted under 35 U.S.C. 154(b) by 0 days.

(21) Appl. No.: 15/225,259

(22) Filed: Aug. 1, 2016

(51) Int. Cl.
*A61M 5/315* (2006.01)
*A61M 5/24* (2006.01)
*G06F 19/00* (2011.01)
*A61M 5/20* (2006.01)

(52) U.S. Cl.
CPC .......... *A61M 5/31551* (2013.01); *A61M 5/24* (2013.01); *A61M 5/31573* (2013.01); *G06F 19/3406* (2013.01); *G06F 19/3456* (2013.01); *A61M 5/20* (2013.01); *A61M 5/3157* (2013.01); *A61M 5/31568* (2013.01); *A61M 2005/2093* (2013.01); *A61M 2205/3584* (2013.01); *A61M 2205/3592* (2013.01); *A61M 2205/50* (2013.01)

(58) Field of Classification Search
CPC .......... A61M 5/31551; A61M 5/31573; A61M 5/31568; A61M 5/3157
See application file for complete search history.

(56) References Cited

U.S. PATENT DOCUMENTS

| | | | | |
|---|---|---|---|---|
| 5,739,775 | A * | 4/1998 | Brandestini | G01D 5/2492 341/10 |
| 6,277,099 | B1 * | 8/2001 | Strowe | A61M 5/31553 604/186 |
| 7,008,399 | B2 * | 3/2006 | Larsen | A61M 5/142 604/65 |

(Continued)

FOREIGN PATENT DOCUMENTS

| | | |
|---|---|---|
| CN | 101862489 A | 10/2010 |
| CN | 102413856 A | 4/2012 |

(Continued)

*Primary Examiner* — Andrew Gilbert
(74) *Attorney, Agent, or Firm* — KramerAmado, P.C.

(57) ABSTRACT

A drug delivery device which includes a first housing part, a second housing part, a button, a drug expelling mechanism, a graduated plate, a circuit board and a pressing rod. The button is connected to the first housing part. The drug expelling mechanism is disposed inside the second housing part, and includes a dose setting member which is rotatable and configured to set a drug dose to be expelled. The graduated plate is disposed inside the first housing part and connected to the button, and includes a first conductive element and a plurality of second conductive element disposed on a surface thereof. The plurality of second conductive elements are arranged in interval and the first conductive element is electrically connected to the plurality of second conductive elements. The circuit board is disposed inside the first housing part and connected to the dose setting member. The pressing rod is inserted through the graduated plate, and includes an end connected to the button and the other end movable on an axial direction to trigger the actuating switch.

21 Claims, 5 Drawing Sheets

(56) References Cited

U.S. PATENT DOCUMENTS

| | | | |
|---|---|---|---|
| 7,749,186 B2* | 7/2010 | Kohlbrenner | A61M 5/20 604/207 |
| 8,052,655 B2* | 11/2011 | Moller | A61M 5/31553 604/246 |
| 8,221,356 B2* | 7/2012 | Enggaard | A61M 5/20 604/152 |
| 8,465,448 B2 | 6/2013 | Andrews | |
| 8,556,847 B2* | 10/2013 | Kohlbrenner | A61M 5/20 604/500 |
| 8,556,866 B2 | 10/2013 | Krulevitch et al. | |
| 8,632,509 B2* | 1/2014 | Moller | A61M 5/31553 604/246 |
| 8,961,463 B2 | 2/2015 | Edhouse et al. | |
| 9,186,465 B2* | 11/2015 | Jorgensen | A61M 5/31551 |
| 9,192,728 B2* | 11/2015 | Gilmore | A61M 5/31551 |
| 9,314,573 B2* | 4/2016 | Nielsen | A61M 5/24 |
| 2006/0224123 A1* | 10/2006 | Friedli | A61M 5/31525 604/207 |
| 2008/0188813 A1 | 8/2008 | Miller et al. | |
| 2008/0243088 A1 | 10/2008 | Evans | |
| 2011/0270214 A1* | 11/2011 | Jorgensen | A61M 5/31551 604/500 |
| 2012/0065588 A1 | 3/2012 | Cirillo et al. | |
| 2014/0121602 A2 | 5/2014 | Ning et al. | |
| 2014/0142512 A1* | 5/2014 | Butler | A61M 5/31525 604/189 |
| 2014/0171879 A1* | 6/2014 | Butler | A61M 5/31525 604/218 |
| 2014/0194825 A1* | 7/2014 | Nielsen | A61M 5/24 604/189 |
| 2014/0194826 A1 | 7/2014 | Nielsen et al. | |
| 2014/0194829 A1* | 7/2014 | Baek | A61M 5/31551 604/207 |
| 2014/0276583 A1* | 9/2014 | Chen | A61M 5/31546 604/506 |
| 2015/0018775 A1 | 1/2015 | Groeschke et al. | |
| 2015/0112272 A1 | 4/2015 | Wendland | |
| 2015/0190583 A1 | 7/2015 | Jones | |
| 2015/0202375 A1 | 7/2015 | Schabbach et al. | |
| 2015/0202376 A1* | 7/2015 | Haupt | A61M 5/24 604/189 |
| 2015/0246179 A1* | 9/2015 | Zur | A61M 5/3157 604/506 |
| 2015/0302818 A1* | 10/2015 | Cowe | A61M 5/31525 604/189 |
| 2015/0343152 A1 | 12/2015 | Butler et al. | |
| 2015/0352288 A1* | 12/2015 | Andersen | A61M 5/20 604/134 |
| 2015/0367077 A1* | 12/2015 | Plambech | A61M 5/1452 604/111 |
| 2016/0001011 A1 | 1/2016 | Cammish et al. | |
| 2016/0008552 A1* | 1/2016 | Madsen | A61M 5/315 604/506 |
| 2016/0015903 A1* | 1/2016 | Madsen | A61M 5/24 604/211 |
| 2016/0263327 A1* | 9/2016 | Radmer | A61M 5/31 |

FOREIGN PATENT DOCUMENTS

| | | |
|---|---|---|
| CN | 102427840 A | 4/2012 |
| CN | 102526833 A | 7/2012 |
| CN | 103702699 A | 4/2014 |
| CN | 204411425 U | 6/2015 |
| EP | 0554996 A1 | 11/1993 |
| EP | 2011531 A2 | 3/2004 |
| EP | 2364742 A2 | 9/2011 |
| EP | 2427236 B1 | 1/2014 |
| TW | 201107004 A | 3/2011 |
| TW | 201402164 A | 1/2014 |
| TW | 201534364 A | 9/2015 |
| WO | 2010139632 A2 | 12/2010 |
| WO | 2012152628 A1 | 11/2012 |
| WO | 2013004844 A1 | 1/2013 |
| WO | 2013164291 A1 | 11/2013 |

* cited by examiner

DRUG DELIVERY DEVICE AND A DRUG INFORMATION DETECTION DEVICE

TECHNICAL FIELD

Various embodiments disclosed herein generally relate to a drug delivery device for injection of a drug and more particularly, but not exclusively, a drug information detection device for detecting drug dosage information.

BACKGROUND OF THE INVENTION

1. Field of the Invention

This invention relates generally to an injection pen device for injection of a drug and a drug information detection device for detecting the quantity of drug injected.

2. Description of Related Art

In the related art, an injection pen (such as an insulin injection pen) is provided for allowing a patient to select a dose and perform self-injection, such that the patient with chronic disease can perform self-treatment at home. Injection pens have significantly improved the lives of patients who must self-administer drugs. There are many different types of injection pens, including simple disposable pens or sturdy multiuse injection pens adapted to be used with pre-filled cartridges. However, regardless of their types, they are useful in assisting patients to self-administer drugs.

The patients with chronic diseases usually must be given drugs according to a predetermined schedule, so a pen-type drug delivery device is developed to provide the patient, who does not have formal medical training, to periodically perform self-injections. A common pen-type drug delivery device includes an injection dose knob and an injection unit, the injection dose knob is configured to adjust and set an injection dose, and the injection unit is configured to inject according to the injection dose set by the injection dose knob. The injection unit generally includes a piston rod configured to expel drug out of the needle for injection. The injection dose adjustment knob can be rotated to a predetermined graduation to set a stroke of the piston rod. When a user presses the injection dose knob, the injection dose knob is rotated and moved downward to push the piston rod to a predetermined location, thereby completing the injection.

Performing the injection at the correct date and time and in the right dosage is critical for managing patient illness. For example, it is very important for a diabetic to inject an adequate dose of insulin at the right time. In order to check the effect of an insulin injection, medical worker usually encourages the diabetic to record the dose and time of every injection. However, the conventional injection device is unable to record the drug dose and injection time of every injection, so the patient must record the data in a written notebook. If the patient forgets to record or records incorrect data, it may mislead the medical worker to make improper drug treatment decisions in the future.

Generally, the injection pen comprises an injection part and an adjusting part configured to determine a dose. The injection part comprises a barrel configured to contain a drug, and a plunger to inject the drug. The adjusting part comprises a sleeve and an adjusting knob, wherein the sleeve is fixed to the barrel and has graduation marks.

As discussed briefly above, the adjusting knob is rotatably connected to one end of the sleeve through a screw thread. The plunger passes through the sleeve and is connected to the adjusting knob. Before injection, the adjusting knob is rotated to drive the plunger to move upward until the adjusting knob reaches a predetermined graduation mark on the sleeve. As such, the movement of the plunger is determined, and a proper drug dose is selected. Thereafter, the adjusting knob is pushed to drive the plunger to move down, so as to push the drug out of the barrel to complete the injection.

Known injection pens can select drug dose, but critical information such as injection time, amounts of injected doses, number of injections cannot be recorded by conventional injection pens. The above information is critical to the patient for treatment and for reference to a physician. Without recording relevant information, the patient may forget the injection time and the number of injections, thereby injecting too many or too few times, to the detriment of the patient.

In the related art, the detection device mostly uses a sensor or optical recognition to detect the moving distance of the plunger, and convert a detection result into electronic data. Since a computation result is directly affected by detection of the moving distance of the plunger, the detection device requires higher accuracy for installation, needs to perform complex operations during detection, and may easily result in detection error. The detection device also cannot meet user's recording requirement.

To reduce the detection error, it would be desirable to provide a device which can accurately record critical data during the administration of the drug by using a scale board which accurately determines the number of rotations of the circuit board to record, log and transmit the critical data.

The foregoing objects and advantages of the invention are illustrative of those that can be achieved by the various exemplary embodiments and are not intended to be exhaustive or limiting of the possible advantages which can be realized. Thus, these and other objects and advantages of the various exemplary embodiments will be apparent from the description herein or can be learned from practicing the various exemplary embodiments, both as embodied herein or as modified in view of any variation that may be apparent to those skilled in the art. Accordingly, the present invention resides in the novel methods, arrangements, combinations, and improvements herein shown and described in various exemplary embodiments.

SUMMARY OF THE INVENTION

A brief summary of various embodiments is presented below. In order to overcome these and other shortcomings of the related art and in light of the present need for an injection pen with a drug information detection device configured to record relevant drug dosage information by measuring the rotation of the circuit board by the scale board, a brief summary of various exemplary embodiments is presented. Some simplifications and omissions may be made in the following summary, which is intended to highlight and introduce some aspects of the various exemplary embodiments, but not to limit the scope of the invention. Detailed descriptions of a preferred exemplary embodiment adequate to allow those of ordinary skill in the art to make and use the inventive concepts will follow in later sections.

According to one exemplary embodiment of the present disclosure a drug delivery device includes a first housing part, a second housing part, a button, a drug expelling mechanism, a graduated plate, a circuit board and a pressing rod. The button is connected to the first housing part. The drug expelling mechanism is disposed inside the second housing part, and includes a dose setting member which is rotatable and configured to set a drug dose to be expelled.

The graduated plate is disposed inside the first housing part and connected to the button, and includes a first conductive element and a plurality of second conductive element disposed on a surface thereof. The plurality of second conductive elements are arranged in interval and the first conductive element is electrically connected to the plurality of second conductive elements. The circuit board is disposed inside the first housing part and connected to the dose setting member. The pressing rod is inserted through the graduated plate, and includes an end connected to the button and the other end movable on an axial direction to trigger the actuating switch. The circuit board includes a grounding element, a signal reading element, a processing unit and an actuating switch. The grounding element is joined with the first conductive element. The signal reading element is rotatable along with rotation of the dose setting member, so as to contact one of the plurality of second conductive elements to read an electric signal. The processing unit is electrically connected to the grounding element and the signal reading element, and configured to determine a rotation amount of the dose setting member according to the electric signal. The actuating switch is electrically connected to the processing unit and configured to drive the processing unit.

In an embodiment of the present disclosure, the drug delivery device further includes a base which is disposed inside the first housing part, wherein the base comprises a holding part and a hollow cylinder inserted through the holding part. The holding part is configured to hold the graduated plate.

In an embodiment of the present disclosure, the drug delivery device further includes a bearing mounted on an outer surface of the hollow cylinder.

In an embodiment of the present disclosure, the drug delivery device further includes a battery disposed inside the first housing part and electrically connected to an input terminal of the circuit board.

In an embodiment of the present disclosure, the button includes a hollow shaft configured to receive the pressing rod therein, and an outer surface of the hollow shaft is joined with an inner surface of the hollow cylinder. The pressing rod is inserted through the hollow cylinder.

In an embodiment of the present disclosure, the graduated plate has a hole which is in communication with the hollow cylinder, the first conductive element is disposed around the hole, and the plurality of the second conductive elements are disposed around the hole.

In an embodiment of the present disclosure, the grounding element includes a ring-shaped part and a plurality of pins connected to the ring-shaped part, and the ring-shaped part is joined with the first conductive element, and the plurality of pins are disposed on the circuit board and electrically connected to the processing unit.

In an embodiment of the present disclosure, the dose setting member includes a dose sleeve and a dose knob which is fixed at an end of the dose sleeve.

In an embodiment of the present disclosure, the drug delivery device further includes a connection member configured to connect the dose setting member and the first housing part. The connection member includes a base part, a link rod and a plurality of hooks. The base part is fixed with the first housing part. The link rod is inserted through the dose knob, and has an end connected to the base part and the other end plugged with a shaft of the dose sleeve. The plurality of hooks are configured to join with the outer surface of the dose knob.

In an embodiment of the present disclosure, the processing unit determines the drug dose to be expelled according to the rotation amount of the dose setting member and generates injection dose information.

In an embodiment of the present disclosure, the circuit board includes a wireless transmission unit configured to transmit the injection dose information to an external electronic device.

According to one exemplary embodiment of the present disclosure a drug information detection device includes a first housing part, a button, a graduated plate, a circuit board and a pressing rod. The button is connected to the first housing part. The graduated plate is disposed inside the first housing part and connected to the button, and includes a first conductive element and a plurality of second conductive element disposed on a surface thereof. The plurality of second conductive elements are arranged in interval and the first conductive element is electrically connected to the plurality of second conductive elements. The circuit board is disposed inside the first housing part and connected to the dose setting member. The pressing rod is inserted through the graduated plate, and includes an end connected to the button and the other end movable on an axial direction to trigger the actuating switch. The circuit board includes a grounding element, a signal reading element, a processing unit and an actuating switch. The grounding element is joined with the first conductive element. The signal reading element is rotatable along with rotation of the dose setting member, so as to contact one of the plurality of second conductive elements to read an electric signal. The processing unit is electrically connected to the grounding element and the signal reading element, and configured to determine a rotation amount of the dose setting member according to the electric signal. The actuating switch is electrically connected to the processing unit and configured to drive the processing unit.

In an embodiment of the present disclosure, the drug delivery detection device further includes a base which is disposed inside the first housing part, wherein the base comprises a holding part and a hollow cylinder inserted through the holding part. The holding part is configured to hold the graduated plate.

In an embodiment of the present disclosure, the drug delivery detection device further includes a bearing mounted on an outer surface of the hollow cylinder.

In an embodiment of the present disclosure, the drug delivery detection device further includes a battery disposed inside the first housing part and electrically connected to an input terminal of the circuit board.

In an embodiment of the present disclosure, the button includes a hollow shaft configured to receive the pressing rod therein, and an outer surface of the hollow shaft is joined with an inner surface of the hollow cylinder. The pressing rod is inserted through the hollow cylinder.

In an embodiment of the present disclosure, the graduated plate has a hole which is in communication with the hollow cylinder, the first conductive element is disposed around the hole, and the plurality of the second conductive elements are disposed around the hole.

In an embodiment of the present disclosure, the grounding element includes a ring-shaped part and a plurality of pins connected to the ring-shaped part, and the ring-shaped part is joined with the first conductive element, and the plurality of pins are disposed on the circuit board and electrically connected to the processing unit.

In an embodiment of the present disclosure, the dose setting member includes a dose sleeve and a dose knob which is fixed at an end of the dose sleeve.

In an embodiment of the present disclosure, the drug delivery device further includes a connection member configured to connect the dose setting member and the first housing part. The connection member includes a base part, a link rod and a plurality of hooks. The base part is fixed with the first housing part. The link rod is inserted through the dose knob, and has an end connected to the base part and the other end plugged with a shaft of the dose sleeve. The plurality of hooks are configured to join with the outer surface of the dose knob.

In an embodiment of the present disclosure, the processing unit determines the drug dose to be expelled according to the rotation amount of the dose setting member and generates injection dose information.

BRIEF DESCRIPTION OF THE DRAWINGS

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

These and other more detailed and specific features of the present invention are more fully disclosed in the following specification, reference being had to the accompanying drawings, in which.

Figure 1:
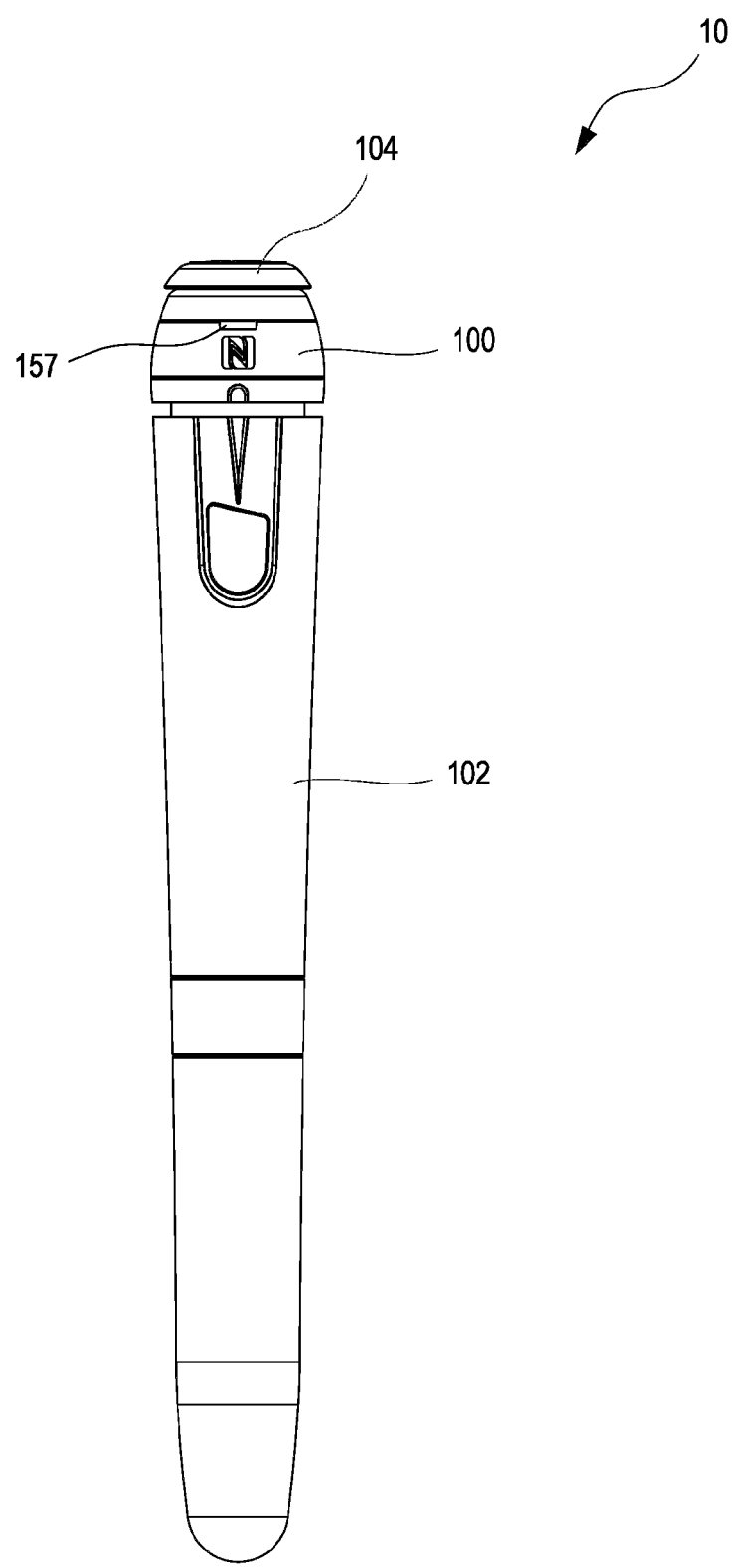
FIG. 1 is an elevational view of the drug delivery device of the present disclosure.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION OF THE INVENTION

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

FIG. 1 is an elevational view of the drug delivery device of the present disclosure. The drug delivery device 10 includes a first housing part 100, a second housing part 102 and a button 104. As shown in FIG. 1, the button 104 is rotatably connected to the first housing part 100. The drug delivery device further includes a light emitting diode (LED) 157 which is a small and powerful semiconductor light source.

Figure 2:
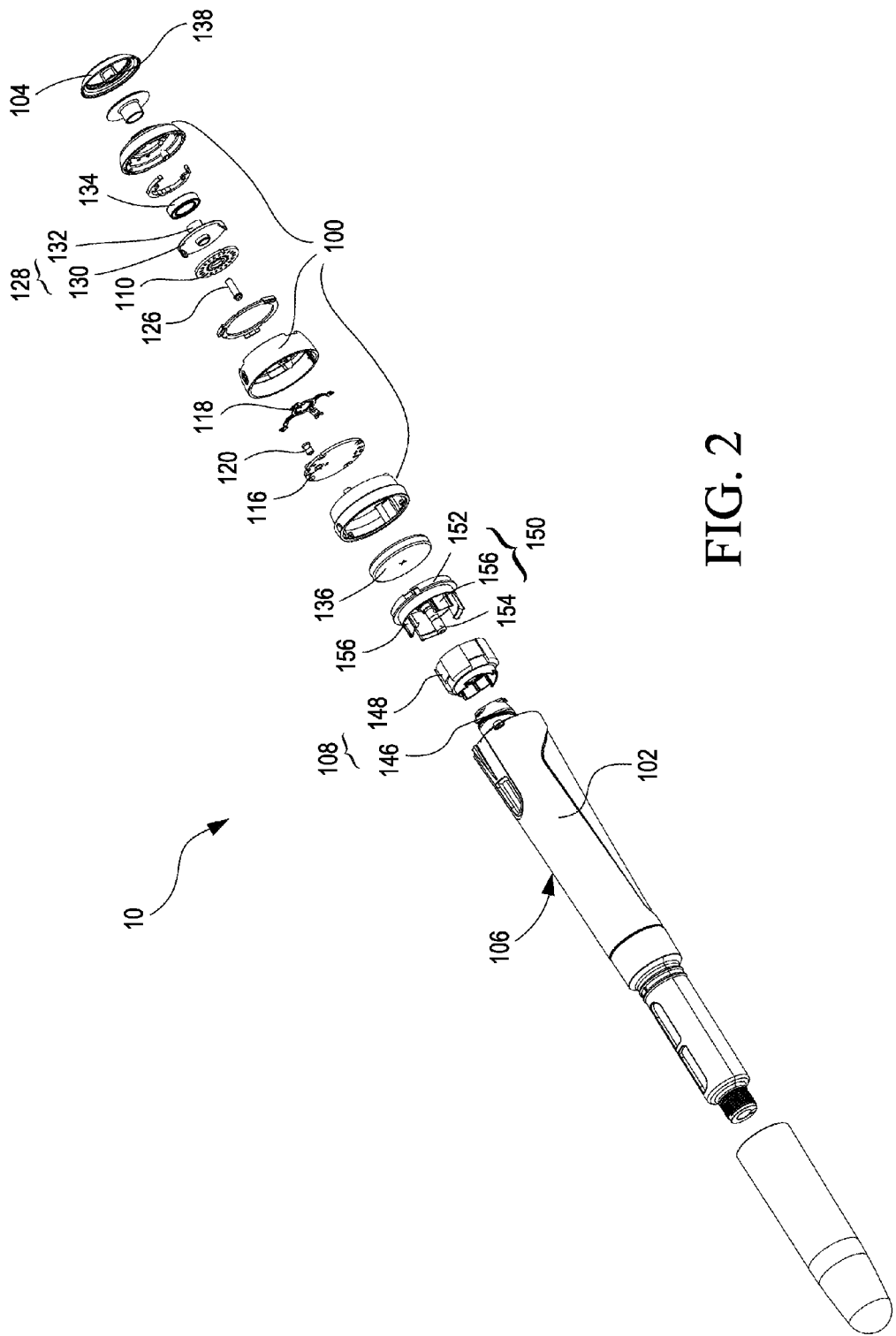
FIG. 2 is an exploded perspective view of the drug delivery device of the present disclosure.

FIG. 2 is an exploded perspective view of the drug delivery device, including a drug expelling mechanism 106, a graduated plate 110, a circuit board 116 and a pressing rod 126.

The drug expelling mechanism 106 is disposed inside the second housing part 102 and includes a dose setting member 108 which is rotatable and configured to set a drug dose to be expelled. The dose setting member 108 includes a dose sleeve 146 and a dose knob 148. The dose knob 148 is fixed at an end of the dose sleeve 146. The drug expelling mechanism 106 further includes a piston rod (not illustrated) which is configured to connect to a piston of a drug cartridge, so as to expel the drug out of needle for injection into a patient. Various alternative and additional beneficial features will be described below.

The graduated plate 110 is disposed inside the first housing part 100 and connected to the button 104. The circuit board 116 is disposed inside the first housing part 100 and connected to the dose setting member 108. The pressing rod 126 is inserted through the graduated plate 110, and has an end connected to the button 104 while the other end is movable in an axial direction to trigger an actuating switch 124 which is positioned on the circuit board 116.

The button 104 being configured to have a hemispherical shape allowing for easier activation of the injection such that pressure can be applied to the button 104 on any edge and continue to have the same quantity of drug being injected. For example, if the patient applies pressure to the edges of the button 104, the same drug amount would be injected, as if the patient applies pressure to the center of the button.

As shown in FIG. 2, the drug delivery device 10 further includes a base 128, a bearing 134, a battery 136 and a connection member 150. The base 128 is disposed inside the first housing part 100, and includes a holding part 130 and a hollow cylinder 132. The holding part 130 is configured to hold the graduated plate 110. The bearing 134 is mounted on an outer surface of the hollow cylinder 132. The battery 136 is disposed inside the first housing part 100 and electrically connected to the circuit board 116. The battery 136 is configured to be non-replaceable such that the drug delivery device 10 is disposed of when the battery 136 has a loss of charge. In an alternative embodiment, the battery 136 is configured to be replaceable when the battery 136 has a loss of charge whereby the patient can remove the battery 136, recharge it, then reinsert the battery 136 into the drug delivery device 10. In an alternative embodiment, the circuit board 116 of the drug delivery device 10 is configured to have disposed thereon an input power terminal (not illustrated) to charge the battery 136.

The connection member 150 is configured to connect the dose setting member 108 and the first housing part 100, whereby the circuit board 116 and the dose setting member 108 are positioned in the first housing part 100 and are connected to each other. Therefore, the circuit board 116 can be rotated with the dose setting member 108.

The connection member 150 includes a base part 152, a link rod 154 and a plurality of hooks 156. The base part 152 is configured to be fixed to the first housing part 100. The link rod 154 is inserted through the dose knob 148, and has an end connected to the base part 152 and the other end plugged with the shaft of the dose sleeve 146. The plurality of hooks 156 are connected to the outer surface of the dose knob 148.

Figure 3:
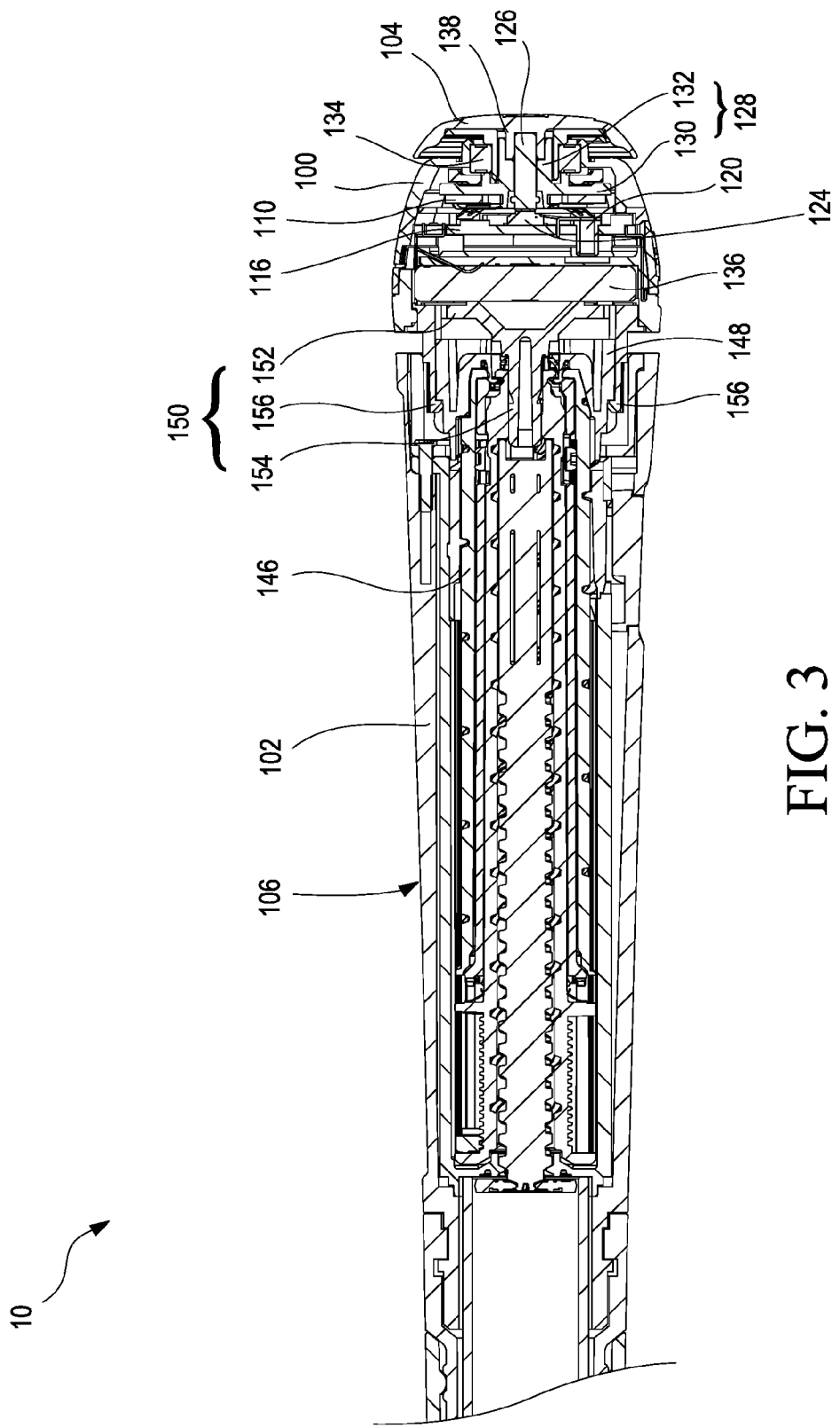
FIG. 3 is a sectional view of the drug delivery device of the present disclosure.

FIG. 3 is a sectional view of the drug delivery device of the present disclosure. The button 104 has a hollow shaft 138 which is configured to receive the pressing rod 126 therein. An outer surface of the hollow shaft 138 is joined with an inner surface of the hollow cylinder 132 of the base 128, so that the button 104 is connected to the graduated plate 110 by the base 128. The pressing rod 126 is inserted through the hollow cylinder 132.

Figure 4A:
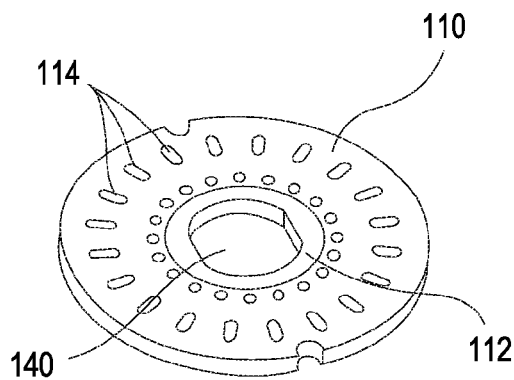
FIGS. 4A through 4C are perspective views of assembly process of some members of the drug delivery device of the present disclosure.
Figure 4B:
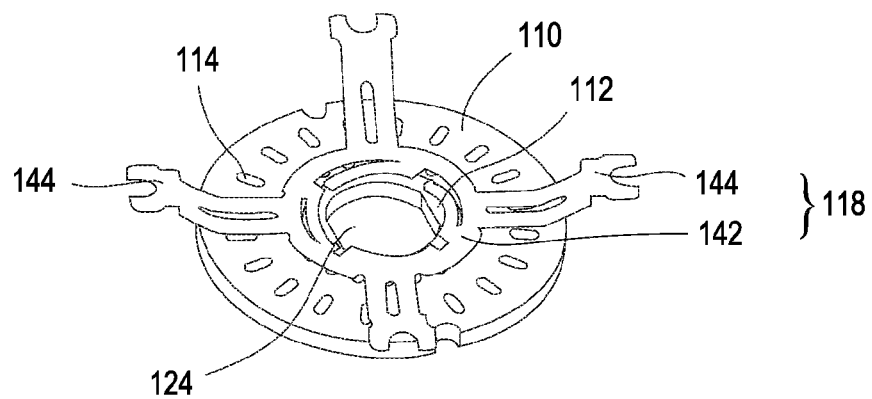
Figure 4C:
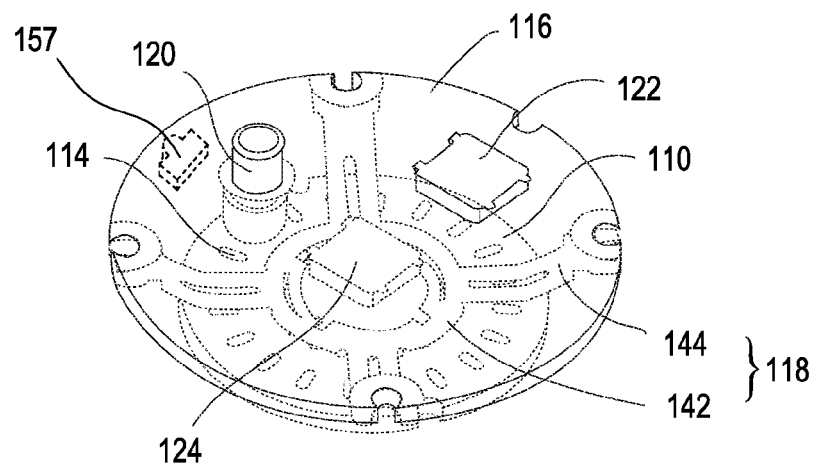

FIGS. 4A through 4C are perspective views of assembly process of some members of the drug delivery device of the present disclosure, for illustrating the connection relationship between the graduated plate 110 and circuit board 116.

As shown in FIG. 4A, the graduated plate 110 has a first conductive element 112 and a plurality of second conductive elements 114 disposed on a surface thereof, and the plurality of second conductive elements 114 are arranged in intervals. The intervals that the conductive elements 114 are arranged are equal in spacing distance. The first conductive element 112 is electrically connected to the plurality of second conductive elements 114. The graduated plate 110 has a hole 140 which is in contact with the hollow cylinder 132 of the base 128. The first conductive element 112 is disposed around the hole 140, and the plurality of second conductive elements 114 are arranged around the hole 140.

As shown in FIG. 4C, the circuit board 116 includes a grounding element 118, a signal reading element 120, a processing unit 122 and the actuating switch 124. The grounding element 118 includes a ring-shaped part 142 and a plurality of pins 144 connected to the ring-shaped part 142. The ring-shaped part 142 of the grounding element 118 is joined with the first conductive element 112 (as shown in FIG. 4B). The plurality of pins 144 are disposed on the circuit board 116 and electrically connected to the processing unit 122. The signal reading element 120 is configured to contact the second conductive elements 114 along with the rotation of the dose setting member 108, so as to read an electric signal. The actuating switch 124 is electrically connected to the processing unit 122 and configured to drive the processing unit 122.

As further shown in FIG. 4C, the actuating switch 124 is aligned with the hole 140 of the graduated plate 110, so that the processing unit 122 can be driven by the actuating switch 124 when the pressing rod 126 passes through the hole 140 to trigger the actuating switch 124 of the circuit board 116. The processing unit 122 is electrically connected to the grounding element 118 and the signal reading element 120, and configured to determine the rotation amount of the dose setting member 108 according to the electric signal from the signal reading element 120.

As further shown in FIG. 4C, the LED 157 is disposed on the circuit board 116 and configured to remain a constant color or blink in a variety of different intervals and different colors to convey information to the patient. For example, the LED 157 will blink red when the battery 136 is low, constant green when the drug delivery device 10 is turned on. Furthermore, the LED 157 will remain a constant color for a predetermined period of time after injection and change after that predetermined period of time has elapsed, indicating that it is safe to operate in order to avoid double dosing.

Each of the plurality of second conductive elements 114 corresponds to one of the rotation amounts of the dose setting member 108, so the signal reading element 120 can read the corresponding electric signal when contacting one of the plurality of second conductive elements 114. The processing unit 122 then calculates the rotation amount of the dose setting member 108 according to the electric signal. Furthermore, the processing unit 122 can determine the drug dose to be expelled according to the rotation amount of the dose setting member 108, and generate injection dose information for the patient.

To reduce and eliminate the incorrect transmission of dosage information, through user or device error, it would be desirable to provide a device with a wireless transmission module to transmit the dosage information to an external device. In an embodiment of the present disclosure, the circuit board 116 can further include a wireless transmission module configured to transmit the injection dose information to an external electronic device which may be smartphone or notebook computer, so as to allow a patient or a doctor to manage the injection dose information. Various alternative and additional beneficial features will be described below.

The drug information (such as injected dose, injection time, injection date, etc.) stored in the control assembly can be transmitted to an external data processing device (such as a tablet computer, a mobile phone, a calculator, a router, etc.) through the wireless transmission module. In practical use, the wireless transmission module can be a Bluetooth module to communicate with a mobile terminal, such as a mobile phone or a tablet computer, for transmitting data periodically or in real time. The drug information can be recorded in the mobile terminal to be shown as diagrams or curves, so to intuitively remind a patient of drug usage. The wireless transmission module can also be a Wi-Fi module to connect to the Internet through a router, and directly transmit the drug information to a computer of a doctor at a local or remote site. Therefore, the doctor can remotely monitor the drug usage of the patient for diagnosis purposes.

In some embodiments, the wireless transmission module can communicate on one or more communication networks including a wide area network (WAN) (e.g., a transport control protocol/internet protocol (TCP/IP) based network, a cellular network, such as, for example, a Long-Term Evolution (LTE) network, a Global System for Mobile Communications (or Groupe Special Mobile (GSM)) network, a General Packet Radio Service (GPRS) network, a Code Division Multiple Access (CDMA) network, an Evolution-Data Optimized (EV-DO) network, an Enhanced Data Rates for GSM Evolution (EDGE) network, a 3GSM network, a 4GSM network, a Digital Enhanced Cordless Telecommunications (DECT) network, a Digital advanced mobile phone system (AMPS) (IS-136/time division multiple access (TDMA)) network, or an Integrated Digital Enhanced Network (iDEN) network, and the like). Furthermore, the one or more communication networks may include a local area network (LAN), a neighborhood area network (NAN), a home area network (HAN), Near-Field Communication (NFC) or personal area network (PAN) employing any of a variety of communications protocols, such as Wi-Fi™, Bluetooth®, and the like.

Figure 5:
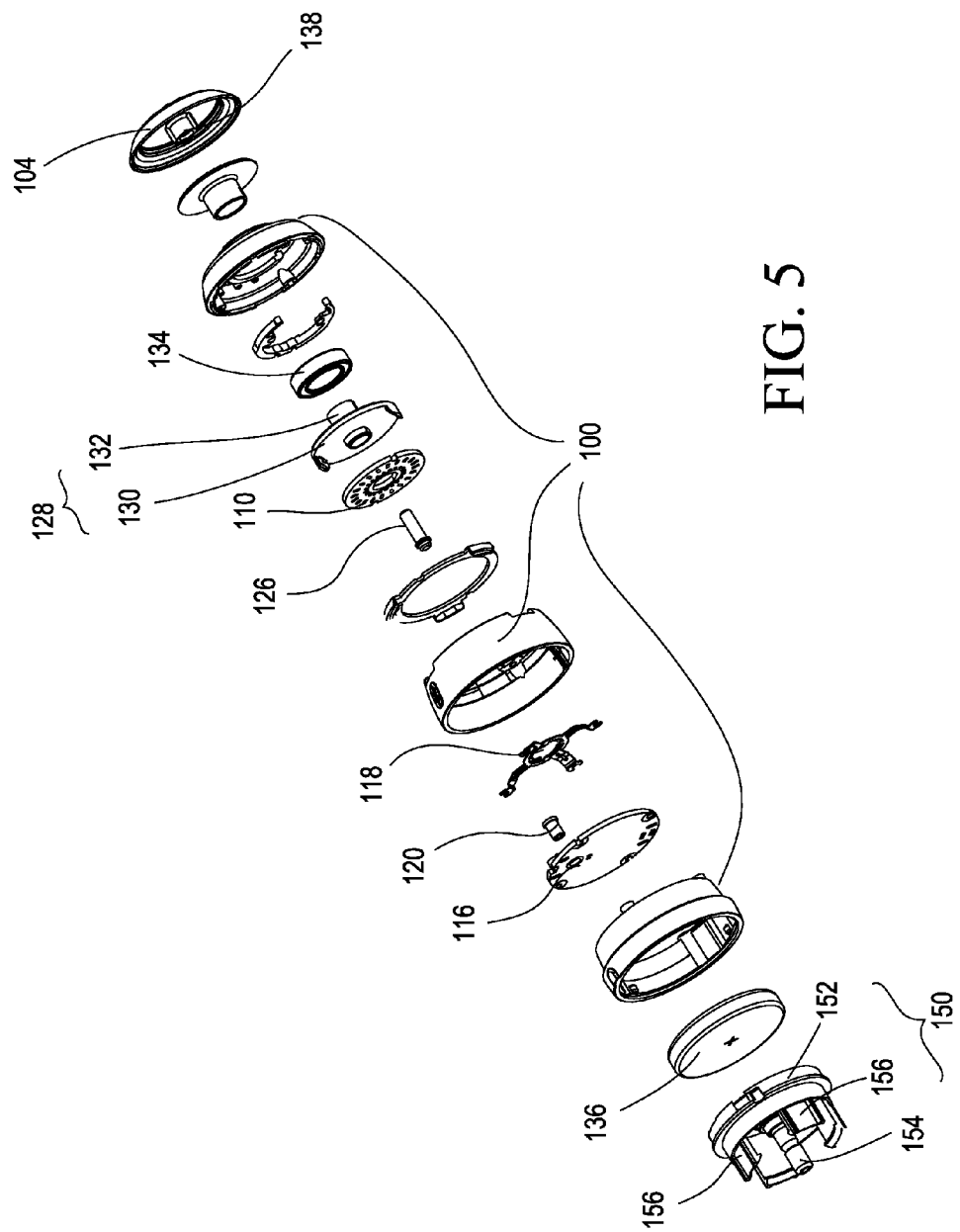
FIG. 5 is an exploded view of the drug delivery detection device of the present disclosure.

FIG. 5 is an exploded perspective view of the drug delivery detection device, including a graduated plate 110, a circuit board 116 and a pressing rod 126.

The graduated plate 110 is disposed inside the first housing part 100 and connected to the button 104. The circuit board 116 is disposed inside the first housing part 100 and connected to the dose setting member 108. The pressing rod 126 is inserted through the graduated plate 110, and has an end connected to the button 104 while the other end is movable in an axial direction to trigger an actuating switch 124 on the circuit board 116.

As shown in FIG. 5, the drug delivery detection device further includes a base 128, a bearing 134, a battery 136 and a connection member 150. The base 128 is disposed inside the first housing part 100, and includes a holding part 130 and a hollow cylinder 132. The holding part 130 is configured to hold the graduated plate 110. The bearing 134 is mounted on an outer surface of the hollow cylinder 132. The battery 136 is disposed inside the first housing part 100 and electrically connected to the circuit board 116.

The connection member 150 is configured to connect the dose setting member 108 and the first housing part 100, whereby the circuit board 116 and the dose setting member 108 are positioned in the first housing part 100 and are connected to each other. Therefore, the circuit board 116 can be rotated with the dose setting member 108.

The connection member 150 includes a base part 152, a link rod 154 and a plurality of hooks 156. The base part 152 is configured to be fixed to the first housing part 100. The link rod 154 is inserted through the dose knob 148, and has an end connected to the base part 152 and the other end plugged with the shaft of the dose sleeve 146. The plurality of hooks 156 are connected to the outer surface of the dose knob 148.

Accordingly, it is to be understood that the above description is intended to be illustrative and not restrictive. Many embodiments and applications other than the examples provided would be apparent upon reading the above description. The scope should be determined, not with reference to the above description or Abstract below, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A drug delivery device, comprising:
    a first housing part;
    a second housing part;
    a button directly in contact with the first housing part;
    a drug expelling mechanism disposed inside the second housing part, and
    a dose setting member which is rotatable and configured to set a drug dose to be expelled;
    a graduated plate disposed inside the first housing part, connected to the button, and comprising a first conductive element and a plurality of second conductive elements disposed on a surface thereof, wherein the plurality of second conductive elements are arranged in interval and the first conductive element is electrically connected to the plurality of second conductive elements;
    a circuit board disposed inside the first housing part and connected to the dose setting member, and comprising:
        a grounding element joined with the first conductive element;
        a signal reading element rotatable along with rotation of the dose setting member, so as to contact one of the plurality of second conductive elements to read an electric signal;
        a processing unit electrically connected to the grounding element and the signal reading element, and configured to determine a rotation amount of the dose setting member according to the electric signal, and
        an actuating switch electrically connected to the processing unit and configured to drive the processing unit;
    a pressing rod inserted through the graduated plate, and having an end directly in contact with the button and the other end directly in contact with the actuating switch and movable on an axial direction to trigger the actuating switch.

2. The drug delivery device according to claim 1, further comprising:
    a base which is disposed inside the first housing part, wherein the base comprises:
        a holding part, and
        a hollow cylinder inserted through the holding part, wherein
        the holding part is configured to hold the graduated plate.

3. The drug delivery device according to claim 2, further comprising a bearing which is mounted on an outer surface of the hollow cylinder.

4. The drug delivery device according to claim 1, further comprising a battery which is disposed inside the first housing part and electrically connected to an input terminal of the circuit board.

5. The drug delivery device according to claim 2, wherein the button comprises:
    a hollow shaft configured to receive the pressing rod therein,
    an outer surface of the hollow shaft configured to connect with an inner surface of the hollow cylinder, and the pressing rod configured to be inserted through the hollow cylinder.

6. The drug delivery device according to claim 2, wherein the graduated plate has a hole which is in communication with the hollow cylinder;
the first conductive element is disposed around the hole, and
the plurality of the second conductive elements are arranged around the hole.

7. The drug delivery device according to claim 1, wherein the grounding element comprises a ring-shaped part and a plurality of pins connected to the ring-shaped part;
the ring-shaped part is joined with the first conductive element; and
the plurality of pins are disposed on the circuit board and electrically connected to the processing unit.

8. The drug delivery device according to claim 1, wherein the dose setting member comprises a dose sleeve and a dose knob which is fixed at an end of the dose sleeve.

9. The drug delivery device according to claim 8, further comprising:
a connection member configured to connect the dose setting member and the first housing part, wherein the connection member comprises:
a base part fixed with the first housing part;
a link rod inserted through the dose knob, and having an end connected to the base part and the other end plugged with a shaft of the dose sleeve, and
a plurality of hooks configured to join with the outer surface of the dose knob.

10. The drug delivery device according to claim 1, wherein the processing unit determines the drug dose to be expelled according to the rotation amount of the dose setting member and generates injection dose information.

11. The drug delivery device according to claim 10, wherein the circuit board comprises a wireless transmission unit configured to transmit the injection dose information to an external electronic device.

12. The drug delivery device according to claim 1, further comprising:
a light emitting diode configured to remain constant and blink.

13. A drug delivery detection device, comprising:
a first housing part;
a button directly in contact with the first housing part;
a graduated plate disposed inside the first housing part and connected to the button, and comprising a first conductive element and a plurality of second conductive elements disposed on a surface thereof, wherein the plurality of second conductive elements are arranged in interval and the first conductive element is electrically connected to the plurality of second conductive elements;
a circuit board disposed inside the first housing part, and comprising:
a grounding element joined with the first conductive element;
a signal reading element rotatable along with rotation of a dose setting member, so as to contact one of the plurality of second conductive elements to read an electric signal;
a processing unit electrically connected to the grounding element and the signal reading element, and configured to determine a rotation amount according to the electric signal, and
an actuating switch electrically connected to the processing unit and configured to drive the processing unit;
a pressing rod inserted through the graduated plate, and having an end directly in contact with the button and the other end directly in contact with the actuating switch and movable on an axial direction to trigger the actuating switch.

14. The drug delivery detection device according to claim 13, further comprising:
a base which is disposed inside the first housing part, wherein the base comprises:
a holding part and a hollow cylinder inserted through the holding part, wherein
the holding part is configured to hold the graduated plate.

15. The drug delivery detection device according to claim 14, further comprising a bearing which is mounted on an outer surface of the hollow cylinder.

16. The drug delivery detection device according to claim 13, further comprising a battery which is disposed inside the first housing part and electrically connected to an input terminal of the circuit board.

17. The drug delivery detection device according to claim 14, wherein the button comprises:
a hollow shaft configured to receive the pressing rod therein,
an outer surface of the hollow shaft configured to connect with an inner surface of the hollow cylinder, and
the pressing rod configured to be inserted through the hollow cylinder.

18. The drug delivery detection device according to claim 14, wherein the graduated plate has a hole which is in communication with the hollow cylinder;
the first conductive element is disposed around the hole, and
the plurality of the second conductive elements are arranged around the hole.

19. The drug delivery detection device according to claim 13, wherein the grounding element comprises a ring-shaped part and a plurality of pins connected to the ring-shaped part;
the ring-shaped part is joined with the first conductive element, and
the plurality of pins are disposed on the circuit board and electrically connected to the processing unit.

20. The drug delivery detection device according to claim 13, wherein the circuit board comprises a wireless transmission unit configured to transmit injection dose information to an external electronic device.

21. The drug delivery detection device according to claim 13, further comprising:
a light emitting diode configured to remain constant and blink.

* * * * *